United States Patent

Imao

[11] Patent Number: 5,291,279
[45] Date of Patent: Mar. 1, 1994

[54] FATIGUE TESTING APPARATUS AND METHOD

[75] Inventor: Akira Imao, Inazawa, Japan

[73] Assignee: Toyoda Gosei Co., Ltd., Nishikasugai, Japan

[21] Appl. No.: 749,676

[22] Filed: Aug. 26, 1991

[30] Foreign Application Priority Data

Aug. 27, 1990 [JP] Japan .................. 2-226011
Nov. 30, 1990 [JP] Japan .................. 2-339013

[51] Int. Cl.⁵ .................................. H04N 7/18
[52] U.S. Cl. ............................. 348/92; 73/799
[58] Field of Search .......... 358/106, 101, 107, 105, 358/93; 73/799; H04N 7/18

[56] References Cited

U.S. PATENT DOCUMENTS

| | | | |
|---|---|---|---|
| 4,158,853 | 6/1979 | Sullivan et al. | 358/93 |
| 4,163,941 | 8/1979 | Linn, Jr. | 358/107 X |
| 4,364,113 | 12/1982 | Sengebush et al. | 358/105 X |
| 4,574,642 | 3/1986 | Fleischman | 73/799 |
| 4,713,686 | 12/1987 | Ozaki et al. | 358/105 X |
| 4,716,459 | 12/1987 | Makabe et al. | 73/799 X |
| 4,893,182 | 1/1990 | Gautraud et al. | 358/105 |
| 4,911,017 | 3/1990 | Marteny | 73/799 |
| 5,047,851 | 9/1991 | Sauerwein et al. | 358/106 X |

Primary Examiner—Victor R. Kostak
Attorney, Agent, or Firm—Cushman, Darby & Cushman

[57] ABSTRACT

A fatigue testing apparatus and method for applying stress to a sample, photographing the degree of fatigue of the sample, and making a material judgment. The sample is deformed by the application of stress thereto. The degree of fatigue of the sample is photographed and recorded as a still image in an intermittent photographing mode using an image photographing device. The photographing timing is synchronized with a peak of the stress applied to the sample. Since the sample deformation at the timing is large, the degree of fatigue of the sample can be photographed accurately. Consequently, it is no longer necessary for the operator in charge to visually check the condition during test such as fatigue test and it becomes possible to confirm cracks, etc. in a real-time manner after the test. Even fine cracks can be checked and so it is possible to make an exact judgment about the degree of fatigue of the sample.

7 Claims, 6 Drawing Sheets

FATIGUE TESTING APPARATUS AND METHOD

BACKGROUND OF THE INVENTION

1. Field of the Invention

The present invention relates to a fatigue testing apparatus and a testing method using the same for applying stress to a sample and photographing the degree of fatigue of the sample to judge the quality of the sample.

2. Description of the Related Art

Fatigue tests per se there are known, for example, such as repeated fatigue tests and ozone exposure tests under stress.

There are known repeated fatigue tests, such as the De Mattia fatigue test, the stretch fatigue test and the flex-stretch fatigue test. The ozone exposure tests under stress, referred to above, there are known a static stretch exposure test and a dynamic stretch exposure test. As other fatigue tests there are heat relaxation breakdown (static stretch) test, rubber vibration insulator durability test, in liquid or oil expansion (linear expansion) test, steering wheel repeated durability test, and stress crack observation (e.g. thermal shock) test.

Out of the above fatigue tests, for example the De Mattia flex fatigue test is performed in accordance with JIS (Japanese Industrial Standard) K6301. During fatigue test such as the De Mattia flex fatigue test, the person in charge visually checks the condition of a sample and judges and records the degree of fatigue thereof at every certain time (e.g. 1 to 2 hours).

According to the above testing method, however, it is impossible to judge an exact generation time of crack, etc. Particularly, in the case of a black sample, it is difficult to find fine cracks or the like at the same time when they are generated.

SUMMARY OF THE INVENTION

Accordingly, it is an object of the present invention to eliminate the necessity for the operator in charge to continue a visual check of the condition of a sample during test such as a fatigue test, and to enable the operator to confirm the occurrence time of cracks in a real-time after test.

It is another object of the present invention to enable the operator to confirm the occurrence of fine cracks, etc. and thereby permit an exact judgment of the degree of material fatigue.

A first feature of the present invention resides in applying stress to a sample to deform the sample and photographing and recording the degree of fatigue of the sample as a still image in an intermittent photographing mode using an image photographing device.

A second feature of the present invention resides in a fatigue testing method comprising steps of applying stress to a sample to deform the sample and photographing and recording the degree of fatigue of the sample as a still image in an intermittent photographing mode using an image photographing device, in which at least the surface to be photographed of the sample is colored in in a color different from the color of the sample.

A third feature of the present invention resides in a fatigue testing apparatus comprising a stress applying means for applying stress to a sample to deform the sample and a photographing and recording means for photographing and recording the degree of fatigue of the sample as a still image in an intermittent photographing mode using an image photographing device.

A fourth feature of the present invention resides in a fatigue testing apparatus comprising a stress applying means for applying stress to a sample to deform the sample, a positioning means for positioning an image photographing device in an opposed relation to the surface to be photographed of the sample, and a photographing and recording means for photographing and recording the degree of fatigue of the sample as a still image in an intermittent photographing mode using the image photographing device.

A fifth feature of the present invention resides in applying stress to a sample repetitively to deform the sample and synchronizing the still image photographing and recording timing with the peak of the stress applied to the sample.

A sixth feature of the present invention resides in a fatigue testing apparatus comprising a stress applying means for applying stress to a sample to deform the sample, a positioning means for positioning an image photographing device in an opposed relation to the surface to be photographed of the sample, and a photographing/recording means for photographing and recording the degree of fatigue of the sample as a still image in an intermittent photographing mode using the image photographing device, in which the still image photographing and recording timing is synchronized with the peak of the stress applied to the sample.

A seventh feature of the present invention resides in that an image photographing device for photographing and recording the degree of fatigue of a sample which has been deformed with stress applied thereto is moved to a predetermined observation position of a sample successively at every predetermined time.

An eighth feature of the present invention resides in a fatigue testing apparatus comprising a stress applying means for applying stress to a sample to deform the sample, a moving means for moving an image photographing device to a predetermined observation position of the sample successively at every predetermined time, and a photographing and recording means for photographing and recording the degree of fatigue of the sample as a still image in an intermittent photographing mode using the image photographing device.

According to the first feature, since the degree of fatigue of the sample which has been deformed with stress applied thereto is photographed and recorded as a still image in an intermittent photographing mode by means of the image photographing device, the degree of fatigue of the stress-deformed sample can be judged in a real-time manner.

According to the second feature, since at least the surface to be photographed of the sample is colored in a color different from the color of the sample, the degree of fatigue of the stress-deformed sample can be recorded in detail.

According to the third feature, stress is applied to the sample by the stress applying means and the sample is deformed thereby. Further, the degree of fatigue of the sample is photographed and recorded as a still image in an intermittent photographing mode by the image photographing device of the photographing and recording means.

Thus, since the stress-deformed sample is photographed and recorded as a still image in an intermittent photographing mode by the image photographing device, the degree of fatigue of the sample can be judged in a real-time manner.

According to the fourth feature, stress is applied to the sample by the stress applying means and the sample is deformed thereby, and the image photographing device is positioned in an opposed relation to the surface to be photographed of the sample by the positioning means. Further, the degree of fatigue of the sample is photographed and recorded as a still image in an intermittent photographing mode by the image photographing device of the photographing and recording means.

Thus, since the image photographing device is positioned opposite to the surface to be photographed of the sample, a predetermined position of the sample is photographed exactly. Further, since the stress-deformed sample is photographed and recorded as a still image in an intermittent photographing mode by the image photographing device, the degree of fatigue of the sample can be judged in a real-time manner.

According to the fifth feature, since the timing of photographing and recording the degree of the repetitive stress-deformed sample as a still image in an intermittent photographing mode by the image photographing device is synchronized with peak of the stress applied to the sample, the deformation of the sample is large and there is photographed a state which represents the degree of fatigue exactly.

According to the sixth feature, stress is applied to the sample by the stress applying means and the sample is deformed thereby, and the image photographing device is positioned opposite to the surface to be photographed of the sample by the positioning means. Further, the degree of fatigue of the sample is photographed and recorded as a still image in an intermittent photographing mode by the image photographing device of the photographing and recording means. Since the photograph timing of the image photographing device is synchronized with peak of the stress applied to the sample, the deformation of the sample is large and there is photographed a state which represents the degree of fatigue exactly.

According to the seventh feature, since the image photographing device for photographing and recording the degree of fatigue of the stress-deformed sample as a still image in an intermittent photographing mode is moved to a predetermined observation position of a sample successively at every predetermined position, the deformation of the sample is large and there is photographed a state which exactly represents the degree of fatigue.

According to the eighth feature, stress is applied to the sample by the stress applying means and the sample is deformed thereby, and the image photographing device is moved to a predetermined observation position of the sample successively at every predetermined time. Further, the degree of fatigue of the sample is photographed and recorded as a still image in an intermittent photographing mode by the image photographing device of the photographing/recording means.

Thus, since the image photographing device is moved to a predetermined observation position successively at every predetermined time, the degree of fatigue can be photographed even with respect to plural samples or even throughout the whole outer peripheral area of a sample. Further, since the stress-deformed sample is recorded as a still image in an intermittent photographing mode by the image photographing device, the degree of fatigue of the sample can be judged in a real-time manner.

DETAILED DESCRIPTION OF THE PRESENTLY PREFERRED EXEMPLARY EMBODIMENTS

Figure 1:
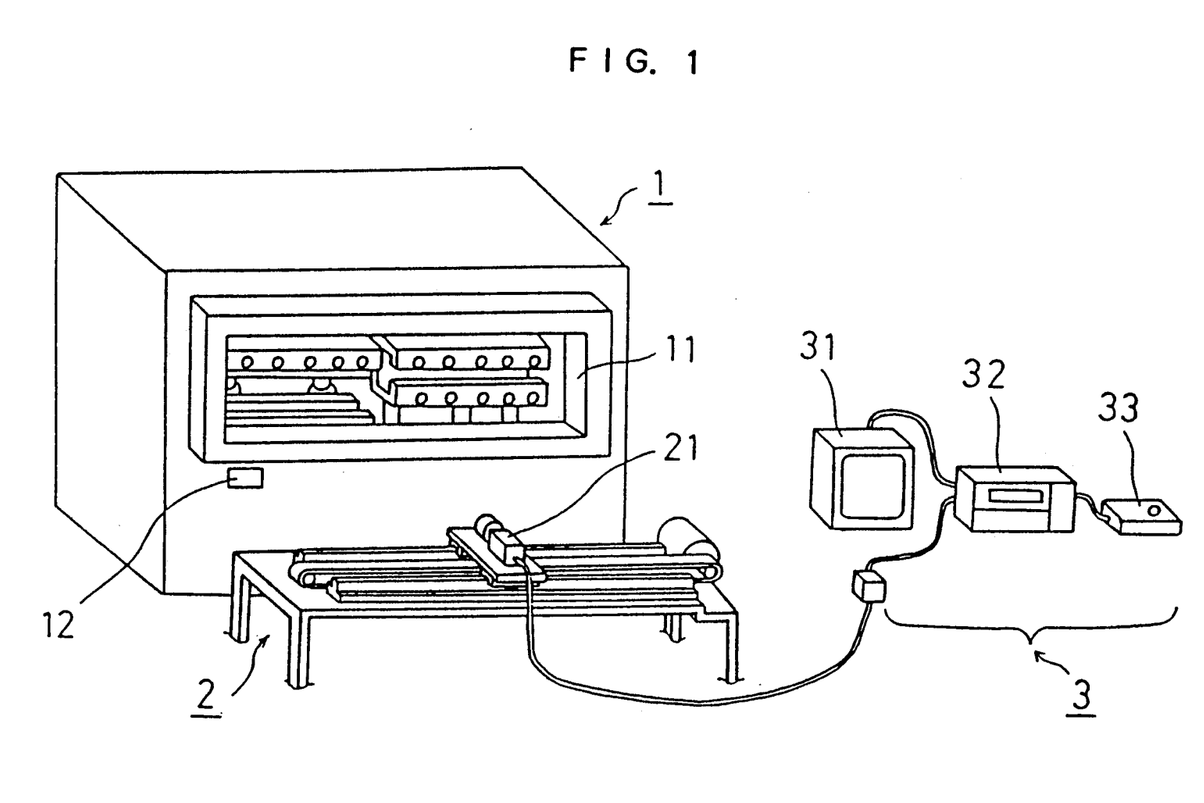
FIG. 1 is an entire construction diagram of a De Mattia flex fatigue testing system as a repeated fatigue tester which employs fatigue testing apparatus and method according to an embodiment of the present invention.

In FIG. 1, a De Mattia device 1 equipped with a constant temperature bath includes a stress applying device. A camera moving device 2 carries thereon a video camera 21 as an image photographing device and includes a positioning device. An automatic observation device 3 includes a photographing and recording device. The De Mattia device 1 with a constant temperature bath, the camera moving device 2 and the automatic observation device 3 constitute a De Mattia flex fatigue testing system as a repetitive fatigue tester.

The De Mattia device 1 with a constant temperature bath is of the following specifications: the frequency is 300 rpm (number of times of bending 5/sec.), the stroke is from 0 to 100 mm, the temperature range is from room temperature to 150 C, and the number of mountable samples is 20.

An observation window 11 of the De Mattia device 1 with a constant temperature bath is constituted by a double glass, and a coating material of silver color that is different from the color of a sample Tp that is applied to at least the surface to be photographed. That is, the side facing the observation window 11, of the sample Tp mounted within the De Mattia device 1 with a constant temperature bath.

Near the observation window 11 is provided a flex counter 12 for counting the number of times of bending.

According to specifications of the camera moving device 2, the camera is fed intermittently, with a camera stop time being 30 seconds (this time being variable). When a camera stop position is determined by proximity switches, a video camera 21 mounted on the camera moving device 2 performs an interval photographing at 0.6 sec. intervals and at a shutter speed of 1/60 sec.

The automatic observation device 3 comprises a monitor television 31 having a monitor size of type 15 and a horizontal resolution of 330 lines, a video deck 32 for exclusive use with still images, and a remote control unit 33 with a jog operation connected to the video deck 32 and being capable of making a delicate adjustment for image feed or return.

In the De Mattia flex fatigue testing system according to the present invention, therefore, it is possible to observe recorded pictures corresponding to about 72 hours in terms of 120 min. video tapes.

Figure 2A:
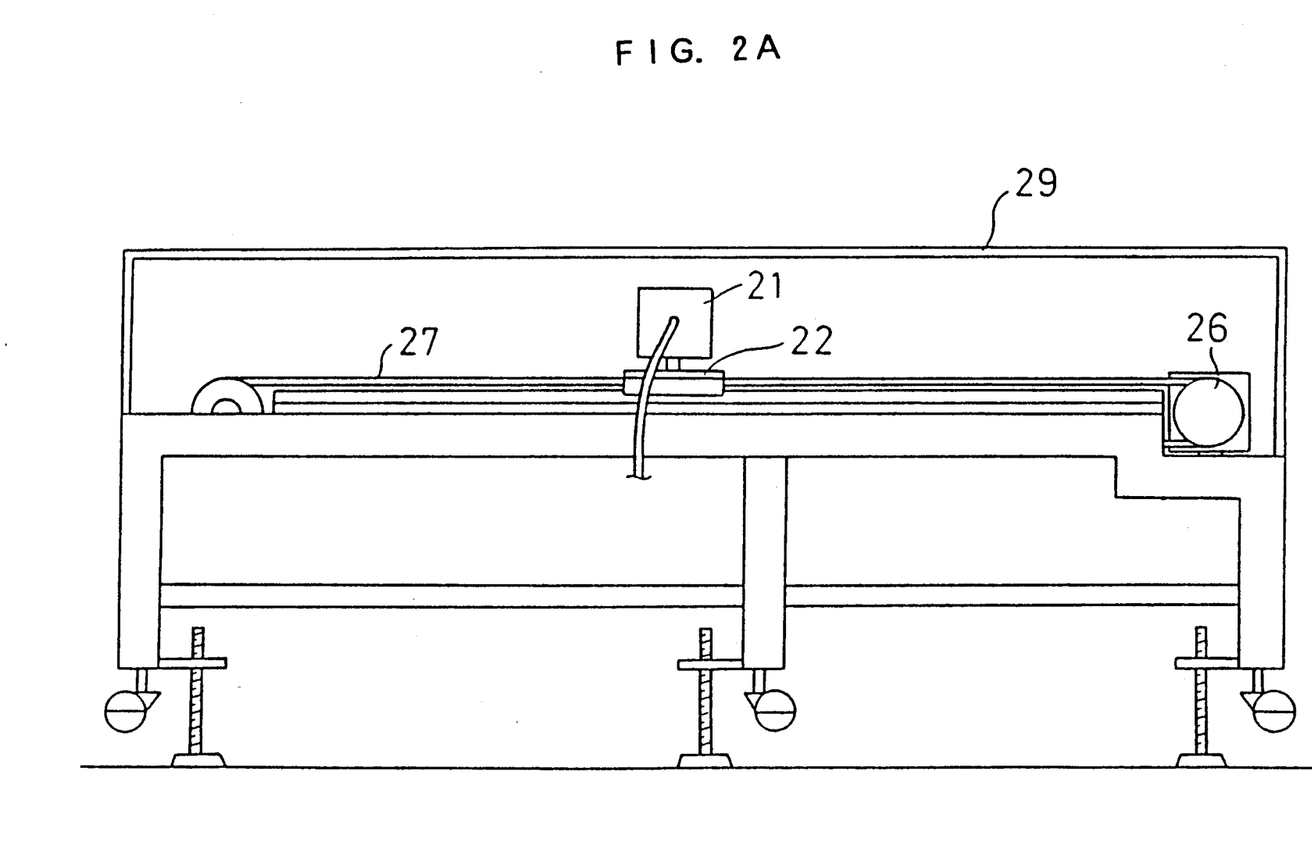
FIG. 2A is a front view showing the details of a camera moving device used in the apparatus embodying the invention.
Figure 2B:
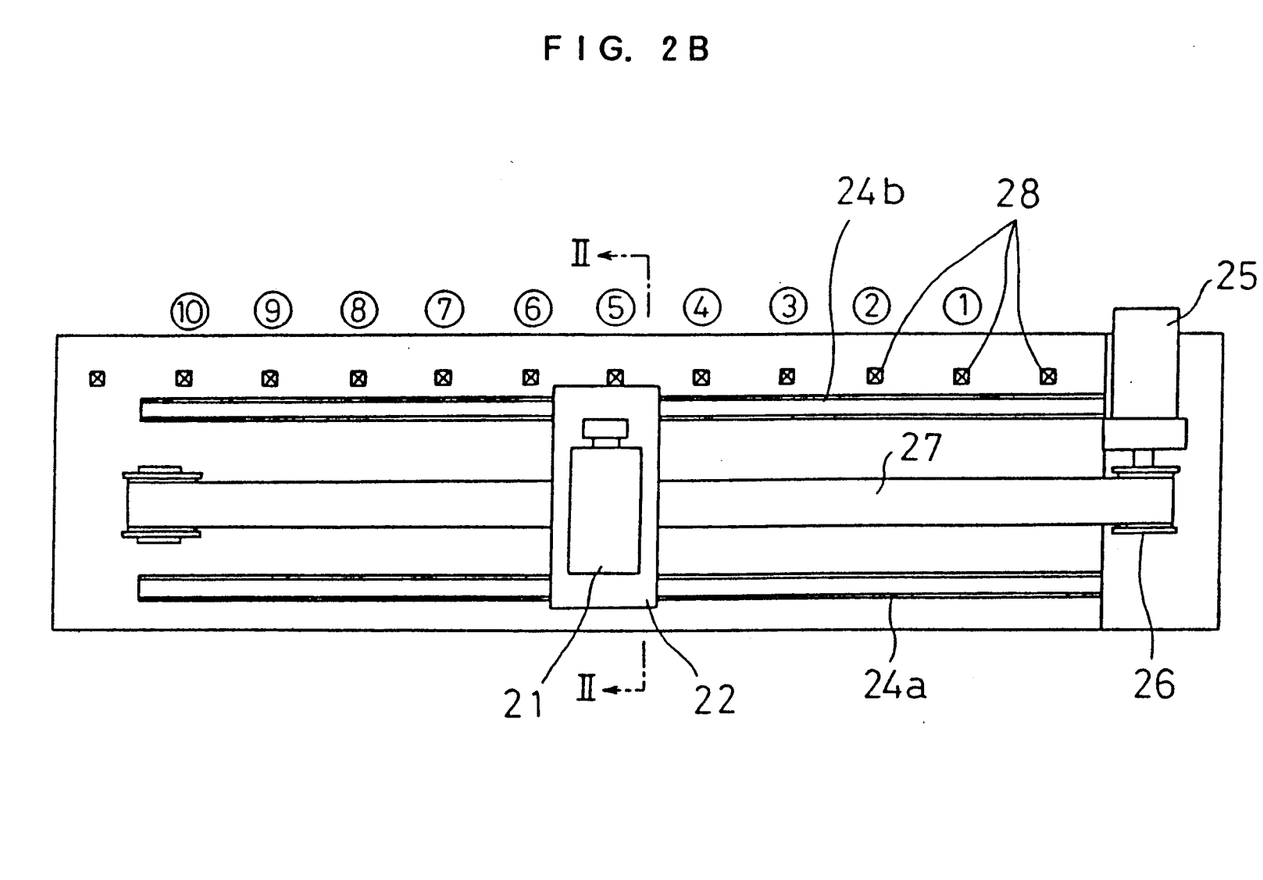
FIG. 2B is a plan view showing the camera moving device a cover of which is removed in FIG. 2A.
Figure 2C:
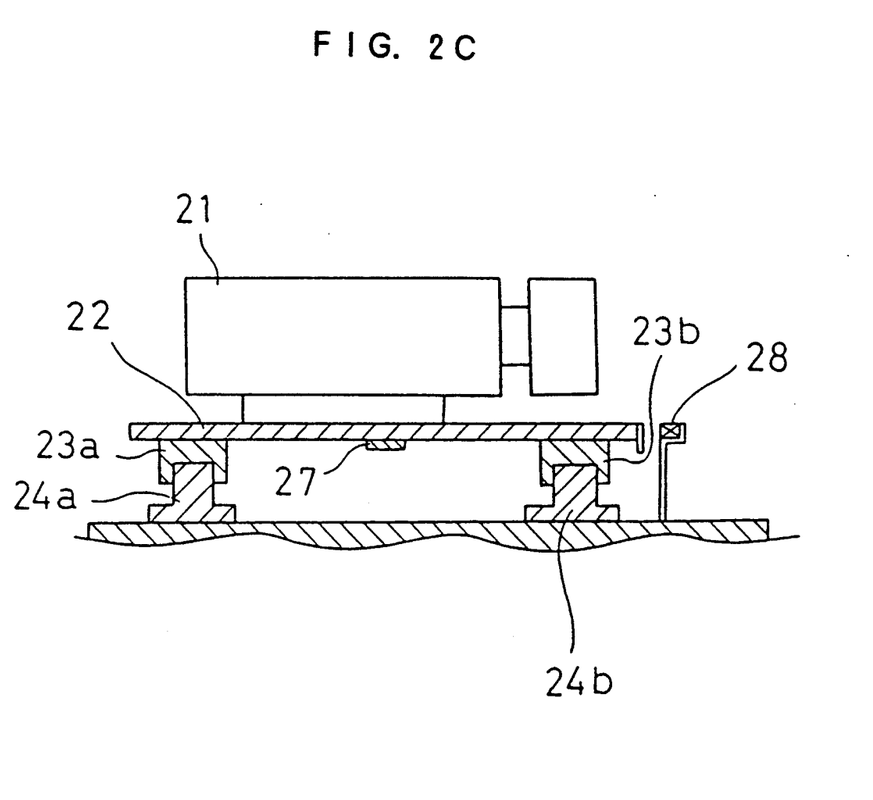
FIG. 2C is a partial vertical sectional view taken along line II—II in FIG. 2B.

The construction of the camera moving device 2 will now be described in detail with reference to FIGS. 2A, 2B and 2C. To a moving base 22 with the video camera 21 mounted thereon are attached two front and rear linear ball bearings 23a, 23b, which are guided by rails 24a and 24b, respectively.

The moving base 22 is moved to the right and left by a geared motor 25 through a pulley 26 and a belt 27.

The position of an end face of the moving base 22 with the video camera 21 mounted thereon is detected and determined by a plurality of proximity switches 28 disposed in advance so that the moving base stops in a position opposed to the sample Tp mounted within the De Mattia device 1 equipped with a constant temperature bath.

Since the moving base 22 of the camera moving device 2 is disposed to move in parallel with the sample Tp mounted in the De Mattia device 1, a focal point of the video camera 21 mounted on the moving base 22 may remain fixed.

In the De Mattia flex fatigue testing system according to the present invention, the video camera 21 is moved to an exact position opposed to each sample Tp in the De Mattia device 1 with a constant temperature bath successively at every predetermined time by means of the camera moving device 2.

Besides, since a coating material of silver color is applied to the surface of each sample Tp, even fine cracks are photographed 50 frames every 0.6 second.

Further, the value on the flex counter 12 is also photographed.

Therefore, by reproducing video tapes after photographing with the automatic observation device 3 while making adjustment with the remote control unit 33 there can be made an exact judgment of cracks in each sample Tp in a real-time manner.

In addition to the above lateral moving pattern of the video camera 21 relative to the samples Tp, the moving pattern may also be vertical or longitudinal in conformity with the direction of arrangement of the samples.

Figure 3:
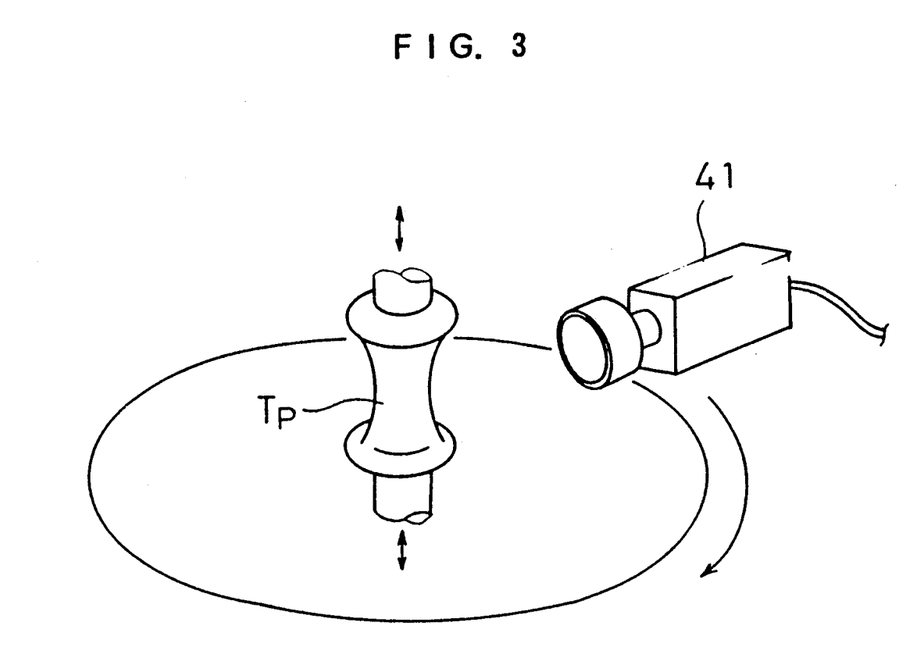
FIG. 3 is an explanatory view showing a camera moving pattern along a circumferential direction.

Further, as shown in FIG. 3, in the case of a rubber vibration insulator as the sample Tp and if it is necessary to photograph the entire outer peripheral area at predetermined observation positions, the moving pattern of a video camera 41 may be set in a circumferential direction so that the video camera is moved to a predetermined observation position of the sample Tp successively at every predetermined time.

Figure 4:
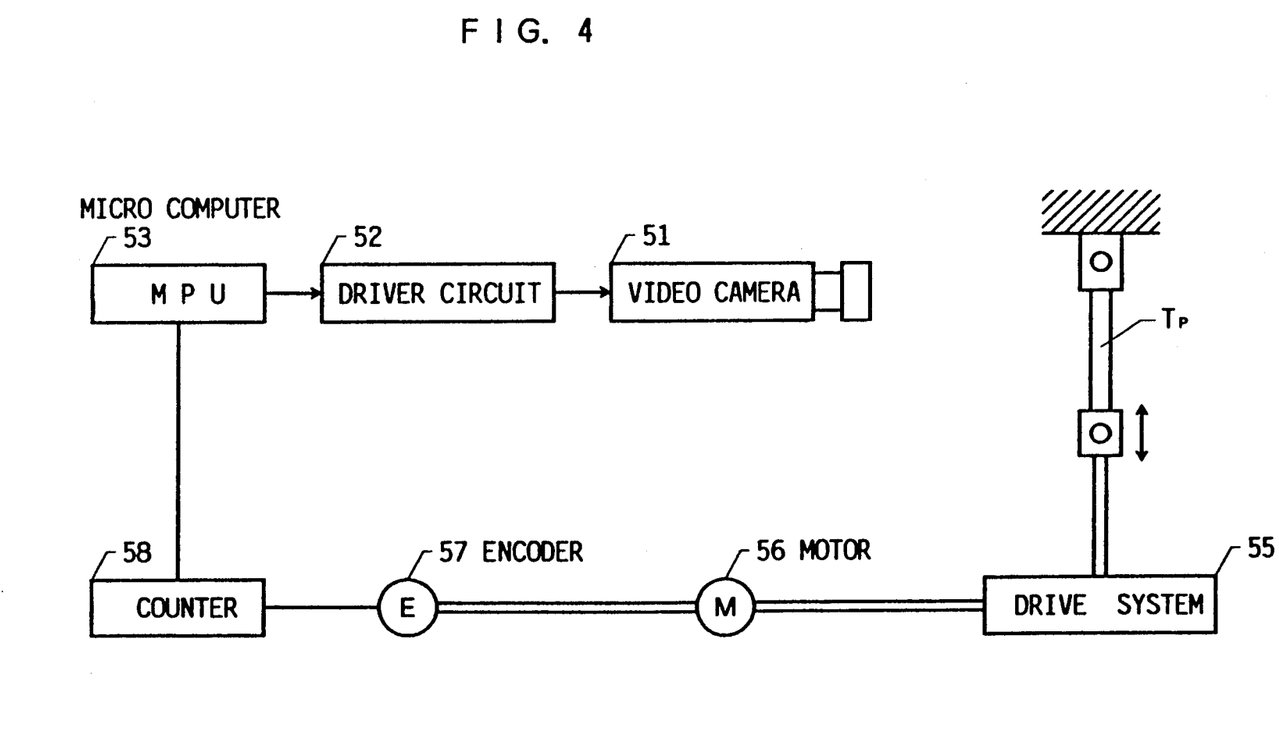
FIG. 4 is a block diagram showing a repeated stretch fatigue testing system capable of a synchronous control which employs fatigue testing apparatus and method according to the present invention.

Referring now to FIG. 4, there is illustrated a construction for synchronous control in a stretch fatigue testing system as a repetitive fatigue tester. A video camera 51 is disposed in an opposed relation to a sample Tp whose upper end is fixed. The video camera 51 is connected to a microcomputer 53 through a driver circuit 52.

On the other hand, a lower end of the sample Tp is a movable end, which is fixed to a drive system 55 such as a cam. The drive system 55 is driven by rotation of a motor 56 to repeat vertical stretching of the lower end of the sample Tp.

An encoder 57 is integrally mounted on an output shaft of the motor 56. An output signal from the encoder 57 is inputted to the microcomputer 53 through a counter 58.

In the stretch fatigue testing system constructed as above, the lower end of the sample Tp is stretched up and down by the motor through the drive system 55. At this time, the output from the encoder 57 attached to the motor 56 is counted by the counter 58 and the count value is inputted to the microcomputer 53. The microcomputer 53 calculates a timing in a most stretched state of the sample Tp, that is, at a peak of the stress applied to the sample Tp, on the basis of the count value from the counter 58. When the microcomputer 53 judges that the timing is obtained, a drive signal is outputted to the video camera 51 through the driver circuit 52.

Therefore, in synchronism with peak of the stress applied to the sample Tp, the degree of fatigue of the sample is photographed and recorded as a still image in an intermittent photographing mode by the video camera 51.

What is claimed is:

1. A fatigue testing method comprising a first step of applying stress to a sample and thereby deforming the sample and a second step of photographing and recording the degree of the stress-deformed sample as a still image in an intermittent photographing mode, wherein the still image is photographed and recorded at a lower frequency than the frequency that the sample is deformed.

2. A fatigue testing method according to claim 1, further including a step of applying a color to at least the surface to be photographed of the sample, said color being different from the color of the sample.

3. A fatigue testing apparatus comprising a stress applying means for applying stress to a sample and thereby deforming the sample and a photographing and recording means for photographing and recording the degree of fatigue of the sample as a still image in an intermittent photographing mode using an image photographing device, wherein the still image is photographed and recorded at a lower frequency than the frequency that the sample is deformed.

4. A fatigue testing apparatus comprising a stress applying means for applying stress to a sample and thereby deforming the sample, a positioning means for positioning an image photographing device in an opposed relation to the surface to be photographed of the sample, and a photographing and recording means for photographing and recording the degree of fatigue of the sample as a still image in an intermittent photographing mode using said image photographing device wherein the still image is photographed and recorded at a lower frequency that the frequency that the sample is deformed.

5. A fatigue testing method comprising a step of holding a plurality of samples in a certain direction to align said samples along a line perpendicular to said direction, a step of applying stress to said samples and thereby deforming said samples, a step of moving an image photographing device along said line keeping a constant distance from surfaces of said samples to position a predetermined observation position of each sample successively at every predetermined time and a step of photographing and recording the degree of fatigue of each of said samples as a still image in an intermittent photographing mode in said predetermined observation position by means of said image photographing device, wherein the still image is photographed and recorded at a lower frequency than the frequency that the sample is deformed.

6. A fatigue testing apparatus comprising a holding means for holding a plurality of samples in a certain direction to align said samples along a line perpendicular to said direction, a stress applying means for applying stress to said samples and thereby deforming said samples, a moving means for moving an image photographing device along said line keeping a constant distance from surfaces of said samples to position a predetermined observation position of each sample successively at every predetermined time, and a photographing and recording means for photographing and recording the degree of fatigue of said samples as a still image in an intermittent photographing mode using said image photographing device, wherein the still image is photographed and recorded at a lower frequency than the frequency that the sample is deformed.

7. A fatigue testing method comprising:

holding a plurality of samples in a certain direction to align said samples along a line perpendicular to said direction;

applying stress to said samples and thereby deforming said samples;

moving an image photographing device along said line keeping a constant distance from surfaces of said samples to position a predetermined observation position of each sample successively at every predetermined time;

photographing and recording the degree of fatigue of each of said samples as a still image in an intermittent photographing mode in said predetermined observation position by means of said image photographing device; and applying a color to at least the surface to be photographed of the sample, said color being different from the color of the sample, wherein the still image is photographed and recorded at a lower frequency than the frequency that the sample is deformed.

* * * * *